United States Patent
Myung et al.

(10) Patent No.: US 11,351,347 B2
(45) Date of Patent: Jun. 7, 2022

(54) VACUUM-ASSISTED DRUG DELIVERY DEVICE AND METHOD

(71) Applicant: VacuMed, LLC., Los Altos, CA (US)

(72) Inventors: David Myung, San Jose, CA (US); Edward E. Manche, Los Altos, CA (US); Donald J. Eaton, Los Altos, CA (US); Anthony J. Abbate, Santa Clara, CA (US)

(73) Assignee: Vacu-Site Medical, Inc., Los Altos, CA (US)

( * ) Notice: Subject to any disclaimer, the term of this patent is extended or adjusted under 35 U.S.C. 154(b) by 459 days.

(21) Appl. No.: 15/331,603

(22) Filed: Oct. 21, 2016

(65) Prior Publication Data

US 2017/0035975 A1    Feb. 9, 2017

Related U.S. Application Data

(63) Continuation-in-part of application No. 14/694,703, filed on Apr. 23, 2015, now Pat. No. 10,426,659.

(Continued)

(51) Int. Cl.
*A61F 9/00* (2006.01)
*A61M 37/00* (2006.01)
(Continued)

(52) U.S. Cl.
CPC ........... *A61M 37/00* (2013.01); *A61F 9/0008* (2013.01); *A61F 9/0017* (2013.01); *A61M 1/00* (2013.01); *A61M 5/14248* (2013.01); *A61M 5/158* (2013.01); *A61M 35/003* (2013.01); *A61M 2037/0007* (2013.01); *A61M 2210/0612* (2013.01)

(58) Field of Classification Search
CPC .... A61M 1/00; A61M 1/0037; A61M 1/0066; A61M 1/0074; A61M 37/00; A61M 35/003; A61M 2210/0612; A61M 2037/0007; A61F 9/0017
See application file for complete search history.

(56) References Cited

U.S. PATENT DOCUMENTS 5,171,215 A * 12/1992 Flanagan .......... A61M 37/0092
                                                    604/20
6,334,856 B1    1/2002 Allen et al.
(Continued)

FOREIGN PATENT DOCUMENTS

DE          100 22 181       11/2001
DE          10022181 A1      11/2011
(Continued)

OTHER PUBLICATIONS

Notification of Transmittal of the International Search Report and the Written Opinion of the International Searching Authority, or the Declaration for International Application No. PCT/US2015/027329 dated Nov. 5, 2015, 18 pages.

(Continued)

*Primary Examiner* — Nathan R Price
*Assistant Examiner* — Anh Bui
(74) *Attorney, Agent, or Firm* — Glen P. Belvis; Belvis Law, LLC.

(57) ABSTRACT

This invention relates to a device and method for the vacuum-assisted delivery of drugs through an intact surface membrane of an organ.

12 Claims, 6 Drawing Sheets

Related U.S. Application Data (60) Provisional application No. 62/244,678, filed on Oct. 21, 2015, provisional application No. 62/138,330, filed on Mar. 25, 2015, provisional application No. 61/983,409, filed on Apr. 23, 2014.

(51) Int. Cl.
  *A61M 5/158* (2006.01)
  *A61M 5/142* (2006.01)
  *A61M 1/00* (2006.01)
  *A61M 35/00* (2006.01)

(56) References Cited

U.S. PATENT DOCUMENTS

| | | | |
|---|---|---|---|
| 6,344,856 | B1 | 2/2002 | Lum et al. |
| 8,915,894 | B1* | 12/2014 | Lonky .................. A61M 37/00 604/290 |
| 9,033,950 | B2 | 5/2015 | Smith et al. |
| 10,426,659 | B2 | 10/2019 | Myung |
| 2005/0197652 | A1 | 9/2005 | Nat |
| 2007/0116752 | A1* | 5/2007 | Chowdhury ......... A61K 9/0097 424/449 |
| 2010/0185048 | A1 | 7/2010 | Lonky et al. |
| 2012/0302972 | A1* | 11/2012 | Higuchi ................ A61F 9/0026 604/290 |
| 2013/0245544 | A1 | 9/2013 | de Juan, Jr. et al. |
| 2015/0045723 | A1* | 2/2015 | Paithankar ............. A61P 17/10 604/22 |
| 2017/0035975 | A1 | 2/2017 | Myung |
| 2020/0113732 | A1 | 4/2020 | Eaton |

FOREIGN PATENT DOCUMENTS

| | | |
|---|---|---|
| WO | WO 2007/131050 | 11/2007 |
| WO | WO 2007/131050 A2 | 11/2007 |
| WO | WO 2014/025796 | 2/2014 |
| WO | WO 2014/025796 A2 | 2/2014 |
| WO | WO 2015/021446 | 2/2015 |
| WO | WO 2015/164626 A2 | 10/2015 |

OTHER PUBLICATIONS

Apr. 23, 2015, PCT, PCT/US2015/027329 Search Report.
Apr. 24, 2015, PCT, PCT/US2015/027329 Written Opinion.
Apr. 8, 2020, EPO, Exam Report Appl No. 15 722 817.2.

\* cited by examiner

VACUUM-ASSISTED DRUG DELIVERY DEVICE AND METHOD

This application claims the benefit of U.S. Application No. 62/244,678 filed Oct. 21, 2015, which is incorporated by reference herein.

This application is also a continuation-in-part of application Ser. No. 14/694,703 filed Apr. 23, 2015 which claims the benefit of U.S. Application No. 61/983,409 filed Apr. 23, 2014 and U.S. Application No. 62/138,330 filed Mar. 25, 2015, all of which are incorporated by reference herein.

FIELD OF THE INVENTION

This invention relates to a non-invasive drug delivery device and method. In particular, it relates to a device for vacuum-assisted drug delivery across unmodified tissue membranes, such as the skin and the epithelium of the eye.

BACKGROUND OF THE INVENTION

There are a multitude of drug delivery methods. Most current methods of drug delivery entail an initial delivery through oral ingestion, inhalation, transmucosal absorption, intravascular injection or intravenous modalities. Some drugs can now be delivered with new technologies, including iontophoresis, ultra-sound and transdermal patches. The most recent advancements have been with targeted drug delivery modalities wherein a targeted release system releases the drug in a dosage form, thereby targeting a localized disease area and reducing the amount of drug taken by the patient. The use of nanoparticles is expected to have a major impact on drug delivery because this small size enables deep access to cells. These new technologies, which provide the initial entry of drugs into the body, have created numerous patient benefits, but there are still opportunities for other types of non-invasive drug delivery techniques. Delivery of drugs that provide effective therapeutic concentrations to targeted tissues, with minimal side effects, is a major challenge because of physiological and anatomical barriers. As an example, the eye is uniquely protected with an epithelial membrane to prevent the entry of foreign bodies such as bacteria from entering the eye socket. In addition, there is a blood barrier surrounding the eye which prevents the migration of molecules from other parts of the body into the eye, whether such molecules comprise diseases or are disease treating entities. As a result of this natural protection, the eye can be extremely difficult to treat. Typically, therapeutic drugs needed for treatment of serious ocular adverse conditions or diseases are delivered with needle injection. This technique poses some risk to the patient, especially when it is necessary to perform multiple injections, such as injecting the drug Avastin into the vitreous for treatment of age-related macular degeneration.

Another type of ophthalmic drug delivery, which is painful to the patient and can sometimes lead to eye infections, is the delivery of drug directly into the cornea. Currently, this procedure normally requires surgical removal of the epithelium. This invasive method is typically used for the delivery of riboflavin into the cornea for purposes of cross-linking corneal collagen tissue. After removing the epithelium, drops of the riboflavin are placed on the corneal surface over a period of time to allow the riboflavin to soak into the corneal tissue. Upon exposure to UVA light, the riboflavin serves as a photosensitizer to create new covalent crosslinks between collagen strands to increase corneal stiffness. Typically it takes 3 to 5 days for re-growth of the epithelium and infections can occur during this period. Moreover, the recovery period is painful to the patient, and there is also risk of haze and scar formation. Despite the fact that corneal collagen crosslinking can be associated with a painful recovery process, it has been clinically proven to manage ectatic corneal disorders such as keratoconus by halting their progression.

Besides ectatic corneal disorders in the anterior segment of the eye, there are numerous other pathological conditions, such as keratoconjunctivitis sicca (KCS), glaucoma, and anterior uveitis which require treatment. KCS, also known as dry eye, is an eye condition caused by inflammation of the cornea and conjunctiva resulting from lack of tear production, causing dryness and pain in those tissues. The KCS condition causes ocular irritation, loss of vision, ocular surface diseases, and the risk of corneal ulceration. Dry eye affects between 10-15% of the US population and is treated primarily with topical drop instillation. However, less than 10% of the instilled eye drop dose is retained on the ocular surface.

Consequently, a drug delivery procedure is needed for the eye, which can: 1) deliver drug quickly and painlessly to the treatment area; 2) do so in a minimally invasive manner, that is, without disrupting the epithelium and 3) improve the residence time for the drug. Such a drug delivery procedure may provide significant medical benefit for patients.

Beyond the need for delivery of drugs into the eye, a significant need also exists for minimally invasive delivery of drugs to other parts of the body. Oral ingestion and injection of drugs, with their respective systemic side effects, are not always safe and practical. For example, a significant obstacle to dermal and transdermal drug delivery is the resilient barrier that the epidermal layers of the skin, primarily the stratum corneum, presents for the diffusion of exogenous chemical agents. Another challenge is the delivery of various therapeutic agents deeper within the skin, such as into the sudoriferous and sebaceous glands or at the base of hair follicles. Further advancement of transdermal drug delivery requires the development of novel delivery systems that are suitable for modern, macromolecular protein and nucleotide therapeutic agents.

The choice regarding a drug delivery modality is dependent on several factors, including the active substance in question, its pharmacokinetic profile, and the desired location of therapeutic action. Having the ability to target a specific location in the body such that a drug is active primarily in the target area, is the ultimate goal of a drug delivery system.

The main advantages of delivering drugs topically include the elimination of first-pass metabolism, sustained drug delivery, reduced frequency of administration, reduced side effects, and improved patient compliance. However, very few drugs are suitable for topical delivery, with passive penetration through skin normally being limited to small molecules (<500 Da), which are neutral and relatively lipophilic. More recently, nanomaterials are increasingly being exploited as carriers to deliver drugs or gene fragments to specific cell targets for therapeutic purposes.

The current invention addresses the need for non-invasive administration of therapeutic agents to a variety of targets including, but not limited to, transdermal administration to the skin and, in particular, topical administration to the epithelium of the eye.

SUMMARY OF THE INVENTION

Thus, in one aspect, this invention relates to a drug delivery device, comprising:

a vacuum source; and
a drug reservoir operatively coupled to the vacuum source; wherein:
the drug reservoir comprises a surface that is conformed to or is conformable with a target surface membrane of an organ to form an air-tight contact between the drug reservoir surface and the target surface membrane and wherein
a fluid within the drug reservoir is in fluid communication with the target surface membrane when the drug reservoir surface is in contact with the target surface membrane.

In an aspect of this invention, the vacuum source is selected from the group consisting of a manual pump, an electric pump and a digitally programmable pump.

The above aspect can include one or any combination of the following aspects.

In an aspect of this invention, the vacuum source is operatively coupled to the drug reservoir via a rigid or flexible tube.

In an aspect of this invention, the drug delivery device further comprises a fluid injection port.

In an aspect of this invention, the fluid injection port is coupled to the drug reservoir or to a rigid or flexible tube that operatively couples the drug reservoir to the vacuum source.

In an aspect of this invention, the fluid in the drug reservoir is in fluid communication with the target surface membrane via a plurality of pores in the drug reservoir surface that is in contact with the target surface membrane.

In an aspect of this invention, the fluid in the drug reservoir is in fluid communication with the target surface membrane via an interconnected or open cell foam material or a porous material, either of which comprises a plurality of channels that extend from a surface of the foam or nanoporous material that is in contact with the fluid in the drug reservoir to the surface of the foam or porous material that is in contact with the target surface membrane.

In an aspect of this invention, the drug delivery device further comprises a proximal or backward flow inhibitor, such as a valve or stepped diffusor, to prevent or reduce the fluid in the drug reservoir from being withdrawn from the drug reservoir when a vacuum is being created by the vacuum source.

In an aspect of this invention, the plurality of pores have a diameter of from about 0.001 mm to about 10 mm.

In an aspect of this invention, the plurality of pores number from 1 to about 1,000,000 pores.

In an aspect of this invention the vacuum source is capable of creating a vacuum from about 760 torr down to about 1 torr.

In an aspect of this invention, the vacuum source can be pulsed to alternatively create and release a vacuum in the drug reservoir when the drug reservoir surface is conformed to and in contact with the target surface membrane.

In an aspect of this invention, the vacuum source can be pulsed between about 1 torr to about 760 torr.

In an aspect of this invention, the vacuum source can be pulsed at a cyclic rate from about 1 second to about 20 minutes.

In an aspect of this invention, the vacuum source can be pulsed at a cyclic rate from about 5 seconds to about 20 seconds.

In an aspect of this invention, the target surface membrane is the epithelium or the conjunctiva of an eye.

An aspect of this invention is a method for delivering a drug into an eye non-invasively for treatment of a disease or condition, comprising:

placing a surface of a drug reservoir in contact with an epithelial or conjunctival surface of the eye to which the surface of the drug reservoir has been conformed such that an air-tight contact between the drug reservoir surface and the epithelial or conjunctival surface is formed and such that a fluid in the drug reservoir is placed in fluid communication with the epithelial or conjunctival surface; and
creating a vacuum within the drug reservoir to effect diffusion of the fluid in the drug reservoir through the epithelial or conjunctival surface and into the subsurface of the eye.

The above aspect can include one or any combination of the following aspects.

In an aspect of this invention, the surface of the eye is the epithelial surface.

In an aspect of this invention, the fluid comprises a substance that is capable of catalyzing the cross-linking of macromolecules in the eye.

In an aspect of this invention, the substance is riboflavin.

In an aspect of this invention, the method is for treatment of a patient in need of treatment of a disease.

In an aspect of this invention, the disease being treated is keratoconus.

In an aspect of this invention, upon delivery of an effective amount of riboflavin to ocular tissue, the eye may be exposed to radiation such as ultraviolet light to crosslink tissue exposed to riboflavin, the riboflavin serving as a photosensitizer to create new covalent crosslinks between collagen strands to increase corneal stiffness.

In an aspect of this invention, the fluid comprises an anti-microbial, an anti-inflammatory, an analgesic or an anti-VEGF drug.

In an aspect of this invention, the delivery of a drug is for the treatment of uveitis, keratoconus, glaucoma, dry eye, diabetic macular edema, age-related macular degeneration, corneal infection or cytomegalovirus retinitis.

In an aspect of this invention, the fluid in the drug reservoir is placed in fluid communication with the epithelium or the conjunctiva of the eye via a plurality of pores in the surface of the drug reservoir.

In an aspect of this invention, the fluid in the drug reservoir comprises a suspension of microparticles or nanoparticles for controlled release of drug or gene therapy in the eye.

In an aspect of the invention, a target area of the vacuum is from 1 to 100 $mm^2$, or more narrowly, 1 to 5 $mm^2$, 5 to 10 $mm^2$, 10 to 20 $mm^2$, 20 to 50 $mm^2$, 50 to 100 $mm^2$, or greater than 100 $mm^2$.

Another aspect of this invention is a method for delivering a drug into an eye non-invasively for treating a disease or condition, comprising: disposing a drug for ameliorating the disease at or near a targeted area of an epithelial or conjunctival surface of the eye; and creating a negative pressure over the targeted area which causes diffusion of the drug through the epithelial or conjunctival surface and into the subsurface of the eye. In one aspect, the negative pressure is localized over the targeted area. These aspects can include one or any combination of the above aspects relating to delivering a drug into an eye.

An aspect of the invention includes a drug delivery device comprising a vacuum source and a drug reservoir operatively coupled to the vacuum source, the drug delivery device for use in treating or ameliorating an eye disease or condition in a patient in need thereof, wherein a surface of a drug reservoir is placed in contact with a target area of a epithelial or conjunctival surface of an eye of the patient to which a surface of the drug reservoir is conformed such that an air-tight contact between the drug reservoir surface and the target area of the epithelial or conjunctival surface is formed and such that a fluid comprising a drug for treating or ameliorating the disease or condition in the drug reservoir is placed in fluid communication with the target area of the epithelial or conjunctival surface and a vacuum is created within the drug reservoir to effect diffusion of the fluid in the drug reservoir through the epithelial or conjunctival surface and into the subsurface of the eye. This aspect can include one or any combination of the above aspects relating to delivering a drug into an eye.

An aspect of this invention is a method for delivering a drug non-invasively through the epidermis, comprising: placing a surface of a drug reservoir in contact with a target area of the epidermis wherein the surface of the drug reservoir is configured to form an air-tight contact between the drug reservoir surface and the epidermal surface and wherein a fluid in the drug reservoir is in fluid communication with the epidermal surface; and creating a vacuum within the drug reservoir to accelerate diffusion of the fluid in the drug reservoir through the epidermis and into target tissue beneath the epidermis.

The above aspect can include one or any combination of the following aspects.

In an aspect of this invention, in the above method, the air-tight contact between the drug reservoir surface and the epidermal surface is aided by an adhesive layer located at a perimeter of the drug reservoir surface, the adhesive layer being placed in contact with the epidermal surface.

In an aspect of this invention, the method is for treatment of a patient in need of treatment of a disease or condition.

In an aspect of this invention, in the above method, the fluid comprises a substance selected from the group consisting of a chemotherapy agent for treatment of skin cancer, an acne drug, a vaccine and a cosmetic substance.

In an aspect of this invention, the vacuum is pulsed to further improve diffusion of the fluid through the epidermis.

In an aspect of this invention, the drug reservoir surface is pliable such that it can conform to movement of the epidermis while maintaining air-tight contact.

In an aspect of this invention, the fluid comprises a drug for the treatment of acne or hair loss.

In an aspect of the invention, the target area is from 10 to 100 mm$^2$.

An aspect of the invention includes a drug delivery device comprising a vacuum source and a drug reservoir operatively coupled to the vacuum source, the drug delivery device for use in treating or ameliorating a skin-related disease or condition in a patient in need thereof, wherein a surface of a drug reservoir is placed in contact with a target area of the surface of an epidermis of the patient to which a surface of the drug reservoir is conformed such that an air-tight contact between the drug reservoir surface and the target area of the epidermal surface is formed and such that a fluid comprising a drug for treating or ameliorating the disease or condition in the drug reservoir is placed in fluid communication with the target area of the epidermal surface and a vacuum is created within the drug reservoir to accelerate diffusion of the fluid in the drug reservoir through the target area of the epidermal surface and into target tissue beneath the epidermis. This aspect can include one or any combination of the above aspects relating to delivering a drug through the epidermis.

Another aspect of this invention is a method for delivering a drug non-invasively through the epidermis for treating a disease or condition, comprising: disposing a drug for ameliorating the disease at or near a targeted area of the epidermis; and creating a negative pressure over the targeted area to accelerate diffusion of the drug through the epidermis and into target tissue beneath the epidermis. In one aspect, the negative pressure is localized over the targeted area. This aspect can include one or any combination of the above aspects relating to delivering a drug through the epidermis. The targeted area can be a small portion of epidermis over a part of the anatomy, such as patch of epidermis on the face, arm, etc.; all or a majority of the epidermis of an anatomical part, such as an arm, face, back, torso, leg, etc., or all or a majority of a human body. Another aspect of this invention is a method for delivering a fluid noninvasively through a surface membrane of an internal organ, comprising: disposing a drug for ameliorating the disease at or near a targeted area on the surface membrane of the internal organ and creating a localized negative pressure over the targeted area to accelerate diffusion of the drug through the surface of the internal organ and into target tissue beneath. In one aspect, the negative pressure is localized over the targeted area. This aspect can include one or any combination of the above aspects relating to delivering a drug through a surface membrane of an internal organ.

An aspect of this invention is a method for delivering a fluid noninvasively through a surface membrane of an internal organ, comprising: accessing the internal organ; placing a surface of a drug reservoir in contact with a target area on the surface membrane of the internal organ wherein the surface of the drug reservoir is configured to form an air-tight contact between the drug reservoir surface and the internal organ membrane surface and wherein a fluid in the drug reservoir is in fluid communication with the internal organ surface; and creating a vacuum within the drug reservoir to accelerate diffusion of the fluid in the drug reservoir through the surface of the internal organ and into target tissue beneath.

In an aspect of this invention, the method is for treatment of a patient in need of treatment of a disease.

In an aspect of this invention, the disease includes cancer, including tumors.

In an aspect of this invention, the cancer includes cancer in the gastro-intestinal tract such as stomach cancer or esophageal tract, colon cancer, liver cancer, lung cancer, pancreatic cancer, brain cancer, bone cancer, oral cancer such as tongue cancer or throat cancer. In these aspects, the drug may be delivered at the site of a tumor present in the anatomy.

In one aspect, the drug is delivered through the serous membrane of an organ, in particular through the visceral membrane and through the parietal layer.

In an aspect of the invention, a target area of the applied vacuum is from 1 to 100 mm$^2$.

In an aspect of this invention, in the above method, the fluid comprises a chemotherapeutic agent for site specific treatment of cancer tumors.

An aspect of the invention includes a drug delivery device comprising a vacuum source and a drug reservoir operatively coupled to the vacuum source, the drug delivery device for use in treating or ameliorating a disease or condition of an internal organ in a patient in need thereof, wherein a surface of a drug reservoir is placed in contact with a target area on a surface membrane of the internal organ of the patient to which a surface of the drug reservoir is conformed such that an air-tight contact between the drug reservoir surface and the target area of the internal organ membrane surface is formed and such that a fluid comprising the drug for treating or ameliorating the disease or condition in the drug reservoir is placed in fluid communication with the target area of the internal organ membrane surface and a vacuum is created within the drug reservoir to accelerate diffusion of the fluid in the drug reservoir through the target area of the surface of the internal organ and into target tissue beneath. This aspect can include one or any combination of the above aspects relating to delivering a drug through a surface membrane of an internal organ.

In one aspect, the present invention includes a device for vacuum-assisted delivery of drug to a target surface membrane of a patient in need of treatment of a disease or condition, comprising: a device body comprising a proximal end and a distal end having fluid communication between the proximal and distal end to allow for creation of a vacuum within the device body; a diffusive membrane at or near the proximal end for contacting with the target surface membrane through which a fluid comprising drug for treating the disease or condition permeates from the device to the target surface membrane when a vacuum is applied to the device, wherein the diffusive membrane provides support to the target surface membrane during application of the vacuum which reduces or prevents damage to the target surface membrane during application of the vacuum, wherein the diffusive membrane is porous to allow permeation of the fluid from the device to the target surface membrane; a proximal flow inhibitor mechanism that reduces or prevents proximal flow of the fluid away from the diffusive membrane during application of the vacuum; and a fluid distributor proximal to the diffusive membrane having a distal surface which provides for uniform distribution and delivery of fluid over an area of the diffusive membrane. The device may include one or any combination of the following aspects and any of the aspects relating to delivery of drug to the eye, epidermis, and internal organs. In one aspect, the device, wherein the distal surface of the fluid distributor comprises protrusions arranged to provide for the uniform distribution and delivery of fluid over an area of the diffusive membrane. In one aspect, the device, wherein the distal surface of the fluid distributor comprises protrusions and when a vacuum is pulled the diffusive membrane is pulled proximally against the protrusions which support the diffusive membrane while maintaining a chamber of uniformly distributed fluid between the fluid distributor and diffusive membrane. In one aspect, the device, wherein the diffusive membrane comprises a plurality of openings that allow for the permeation of drug to the target surface membrane and application of vacuum to the target surface membrane, wherein the number of openings is 100 to 1 million. In one aspect, the device, wherein the proximal flow inhibitor mechanism comprises a uni-directional valve or stepped geometry proximal to the diffusive membrane. In one aspect, the device, wherein an area of a surface of the diffusive membrane for contacting the target surface membrane is 1 $mm^2$ to 1000 $mm^2$. In one aspect, the device, wherein a surface of the diffusive membrane is curved to conform to the target surface membrane. The surface of the diffusive membrane may be concave, convex, or a combination thereof. In one aspect, the device, wherein the device body includes a vacuum port for coupling the device to a vacuum source.

One aspect of the invention includes a method for delivering a drug into the skin of a patient for treating a disease or condition in the patient in need thereof, comprising: placing a surface of a drug reservoir in contact with a skin surface to which the surface of the drug reservoir forms an air-tight contact and such that a fluid in the drug reservoir is placed in fluid communication with the skin surface; and creating a vacuum within the drug reservoir to effect diffusion of the fluid in the drug reservoir through the skin surface and into a subsurface of the skin. The aspect includes one or more of the following aspects: the drug is delivered into a sebaceous gland; the drug is delivered through epidermal, dermal, and/or subcutaneous layers of the skin; the drug is delivered into a bloodstream of the patient; the drug is delivered into a sweat gland; a vacuum is used to increase extracellular space and/or pore sizes within the skin prior to drug diffusion into the skin.

DETAILED DESCRIPTION OF THE INVENTION

Brief Description of the Drawings

The figures herein are presented to aid in the understanding of the invention and are not intended nor should they be construed as limiting the scope of this invention in any manner. Thus, while the figures as such are directed to a device for vacuum-assisted non-intrusive delivery of a drug to the eye and the skin, it is understood that the figures may be modified in ways based on the disclosures herein to adapt to the vacuum-assisted, non-invasive delivery of drugs through the outer layer of any organ.

DISCUSSION

It is understood that, with regard to this description and the appended claims, reference to any aspect of this invention made in the singular includes the plural and vice versa unless it is expressly stated or unambiguously clear from the context that such is not intended. For instance, reference to a "substance" is to be construed as relating to a single substance or to two or more substances. Likewise, reference to a "plurality" is to be construed as referring to one as well as more than one of the elements referred to as a plurality.

As used herein, any term of approximation such as, without limitation, near, about, approximately, substantially, essentially and the like, mean that the word or phrase modified by the term of approximation need not be exactly that which is written but may vary from that written description to some extent. The extent to which the description may vary will depend on how great a change can be instituted and have one of ordinary skill in the art recognize the modified version as still having the properties, characteristics and capabilities of the word or phrase unmodified by the term of approximation. In general, but with the preceding discussion in mind, a numerical value herein that is modified by a word of approximation may be equal to the stated or numerical value or vary from the stated numerical value by ±10%, unless expressly stated otherwise.

The terms "proximal" and "distal" simply refer to the opposite ends of a construct and are used as a method of orienting an object with relation to another object such as the orientation or position of an end the drug delivery device closest to the user of this invention with a portion of the device furthest from the user and closest to the anatomy. For example, proximal may refer to toward or nearest the user of the device while distal may refer to away or furthest from the user of the device or closest to the anatomy being treated. In general, which end is designated as proximal and which as distal is purely arbitrary unless the context unambiguously expresses otherwise.

As used herein, the use of "preferred," "preferably," or "more preferred," and the like refers to preferences as they existed at the time of filing of this patent application.

As used herein, the term "eye" refers to both anterior and posterior segments thereof.

As used herein, the term "subject" refers to mammalian subjects, preferably humans. Mammals include, but are not limited to, primates, farm animals, sport animals, cats, dogs, rabbits, mice, and rats. A human subject may also be referred to as a patient in need of treatment of a condition or disease.

As used herein, the terms "drug", "therapeutic agent", "fluid", and "solute" are used interchangeably and refer to any substance that is delivered using the vacuum delivery system of this invention.

As used herein, the term "apparatus" and "device" are used interchangeably and refer to the vacuum source and drug reservoir that provide delivery of a solute into tissue. It also may refer to a handle which may be part of the vacuum source or a separate entity that is coupled to the vacuum source, the drug reservoir or to both the vacuum source and the drug reservoir.

As used herein, "vacuum" refers to a negative pressure.

A treatment can be, but it not limited to, curative, combative, palliative, ameliorative, or preventative to a disease, condition, or disorder.

All aspects of the present invention relating to delivering a drug include, but are not limited to, delivery of a therapeutic dose of the drug or an effective dose of the drug.

As used herein, "negative pressure" refers to a pressure less than ambient pressure or ambient atmospheric pressure at an altitude above sea level. Negative pressure may also refer to a pressure less than 760 torr.

As used herein, "positive pressure" refers to a pressure greater than ambient or ambient atmospheric pressure at an altitude above sea level. Positive pressure may also refer to a pressure greater than 760 torr.

"Ambient" may refer to the surroundings of a treatment of a patient or a portion of a body of a patient that includes an area to be treated.

As used herein, "localized" may refer to restricted completely or approximately to a particular place or portion of the thing it modifies.

As used herein, a "vacuum source" refers to any device suitable for generating a vacuum within a selected range. The vacuum source may be a vacuum pump, which may be manual, that is hand operated, or it may be electrically operated. It may also be digitally programmable. The vacuum source also refers to a syringe that, when a surface at the end of the syringe is placed in air-tight contact with a membrane surface, can generate a vacuum simply by withdrawing the barrel of the syringe.

As used herein, a vacuum source that is capable of being "pulsed" or "pulsated" refers to such source wherein it is possible to create and release a vacuum in a controlled manner to alternatively apply to a membrane surface a negative pressure at one vacuum level and then to release, partially to a lesser negative pressure or substantially totally near to atmospheric pressure, the vacuum to a different vacuum level and then to repeat the process, going back to the greater negative pressure. The process of going from one negative pressure to another negative pressure and then back again is referred to herein as a "cyclic" application of a vacuum. A single cycle, that is, going from a first negative pressure to a second negative pressure and back again to the first negative pressure, referred to herein as the "cyclic rate" can take from about 1 second to about 20 minutes, preferably at present, from about 5 seconds to about 20 seconds, about 10 seconds to about 15 seconds.

The vacuum source may pulsate the pressure using a controller configured to pulsate the pressure from one negative pressure and a higher pressure and back. A controller may include, for example, a rheostat which is an adjustable resistor that adjusts the current to adjust the speed of the motor of the vacuum pump. The controller may, for example, control the diaphragm of a vacuum pump.

As used herein, a "drug reservoir" refers to an enclosed chamber that is coupled to a vacuum course and that contains a solute or fluid that is to be diffused through a target surface membrane of an organ.

As used herein, an "organ" refers to any bodily organ including, but not limited, the intact surface of external organs such as the eye and the skin and the intact outer surface of internal organs.

As used herein, the terms "solute," and "fluid" are used interchangeably and refer to a liquid that contains a pharmacologically active substance, which may be dissolved or suspended in the liquid.

As used herein, the terms "nozzle," and "drug reservoir surface" are used interchangeably and refer to an end portion of the drug reservoir that is placed in contact with the membrane surface through which a fluid is to be diffused and which includes a plurality of channels through which a liquid containing a pharmacologically active material may pass from the drug reservoir to the target surface membrane.

As used herein, a "port," a "pore," and a "channel" all refer to a passage through a thickness of material that permits a fluid to cross from one side of the thickness of material to the other side of the thickness of material.

This invention relates to an apparatus for the non-invasive delivery of therapeutic drugs across intact membranes and into body tissues. In addition, the apparatus can facilitate the movement and further penetration of drugs already implanted into or already present in body tissues. The drugs can be in the form of small molecules, chemicals, antibiotics, antivirals, peptides, proteins, glycoproteins, markers, therapeutic agents, carbohydrates or other bio-macromolecules (such as gene-therapy agents), macromolecules, micelles, or nanoparticles, and the membranes can be the covering of the eye (e.g., epithelium), the skin (e.g. stratum corneum), subcutaneous tissues, muscle viscera, glands, cellular barriers, plus various other body tissues, as well as benign or malignant neoplasms. The drug delivery process used for penetrating these membrane surfaces, while allowing such surfaces to maintain their respective cellular integrity, is a novel localized application of vacuum that may create negative and/or positive pressure. The negative pressure of the process may be used in combination with a positive pressure. This vacuum mediated pressure may be applied in varying degrees that is constant or pulsated and, as an adjunct, such pressure may be combined with an application of varying temperatures (e.g. heat or cold), and/or vibration, which may be applied prior or subsequent to the pressure. The vacuum mediated pressure can be used with adjunct penetration enhancers, which include but are not limited to, chemicals such as alcohol, acetones, and various organic acids. An energy source can also be applied, such as a light source (e.g. UV light or other wavelengths of light) or radiative heat. It may also be combined with other modalities for drug delivery, such as iontophoresis. Included in the description are therapeutics which may provide medical treatments or which may serve as essential ingredients for creating medical treatments.

The present invention includes a vacuum mediated drug delivery system for delivering various solutes into body tissue without adversely disrupting the exterior surface membrane of the body where the entry is performed. An example of adverse disruption to the body's protective membranes is the physical debridement of the epithelial surface of the eye with a blade, scalpel, or spatulated instrument that is sometimes done to improve the penetration of a topically applied drug into the eye. This invention augments the body's natural diffusion processes, in particular, the diffusion of substances in contact with a body tissue surface through the tissue surface and into the subsurface region. The invention has at least one characteristic wherein a surface vacuum is created at the area of drug entry, generating a negative pressure gradient that does not damage tissue or organs, and causing the drug placed on the surface to diffuse into the targeted area from the area of drug entry.

There are several challenges to delivering a drug with a vacuum to a target surface membrane from the surface of a drug reservoir. The vacuum pressures used to enable or accelerate diffusion of drug through the outer surface of the eye, epidermis, or internal tissues can easily damage the target tissue. Another challenge is ensuring uniform distribution of drug for uniform delivery of drug across the target surface. Another is to reducing or preventing backflow of drug from the drug reservoir into the vacuum pump. The device of the present invention keeps target tissue supported so it is not damaged during the drug delivery process. The present invention may include one or more aspects to address these challenges.

One aspect that addresses these challenges is that the device may include a diffusive membrane that comes in direct contact with the target surface membrane or treated tissue. The diffusive membrane provides supports to the tissue while under significant vacuum. Vacuum ranges applied can easily damage tissue if not adequately supported. In order to provide support while providing delivery of drug across a target surface membrane, the device membrane may include of a porous surface that allows permeation of drug from the device to the tissue. The device membrane may include a series of holes, ports, or openings that allow for the exchange of drug and vacuum while supporting the tissue. The holes, ports, openings are configured to be of a size that allows for fluid transfer while simultaneously supporting tissue under the significant vacuum. Thus, it may be preferable to have a high number of pores with a small surface per hole to provide sufficient drug delivery and support to tissue. It is expected the smaller the surface area of tissue per hole exposed to vacuum, the lower the likelihood of disruption of tissue. For example, the membrane, as described in more detail below, can include a 100 to a million or more pores depending on the treated tissue.

Another aspect that addresses these challenges is a proximal flow inhibitor mechanism that reduces or prevents backflow of drug into the vacuum pump. Such a mechanism may include a serious of geometries to inhibit the flow of liquid/drug into the vacuum pump, for example, a stepped geometry or a unidirectional flow valve.

To further address these challenges, a drug reservoir of a device may further include a structure proximal to the diffusive membrane having a distal surface with protrusions arranged to ensure uniform drug and vacuum delivery over a given surface area. The protrusions act as spacers arranged to distribute drug uniformly across the surface and also act as standoffs. When a vacuum is pulled the diffusive membrane is pulled proximally against the protrusions or standoffs. The protrusions or standoffs support the diffusive membrane while maintaining a chamber of uniformly distributed drug between the structure and diffusive membrane. The drug reservoir also permits the exchange/flow of drug during the process. The drug can be added to the reservoir during the process. This can be for the purpose of recharging the reservoir or circulating with fresh drug. The protrusions or standoffs fix the reservoir space between the diffusive membrane and the upper boundary of the drug reservoir so drug delivery can remain constant even if the surface of the membrane is conformed around a contoured targeted surface membrane.

The target surface membrane of the eye can correspond to the cornea or portion thereof, the sclera or portion thereof, the entire front of the eye, the back of the eye, or the front and back of the eye. The target surface area can range from 1 $mm^2$ to 8000 $mm^2$, more narrowly, 1 to 3 $mm^2$, 1 to 10 $mm^2$, 3 to 10 $mm^2$, 10 to 20 $mm^2$, 20 to 100 $mm^2$, 100 to 1000 $mm^2$, 1000 to 4000 $mm^2$, 4000 to 8000 $mm^2$.

The target surface are of the epidermis can be a small portion of epidermis over a part of the anatomy, such as patch of epidermis on the face, arm, etc.; all or a majority of the epidermis of an anatomical part, such as an arm, face, back, torso, leg, etc., or all or a majority of a human body. The target surface area can range from 1 $mm^2$ to 4 $m^2$, or more narrowly, 1 to 3 $mm^2$, 1 to 10 $mm^2$, 3 to 10 $mm^2$, 10 to 20 $mm^2$, 20 to 100 $mm^2$, 100 to 1000 $mm^2$, 1000 to 10000 $mm^2$, 10000 to 100000 $mm^2$, 100000 $mm^2$ to 1 $m^2$, 1 to 4 $m^2$.

The target surface membrane of an internal organ can correspond to a small area, for example, a location of a tumor, a large portion, or a majority or entire organ area. The target surface area can range from 1 $mm^2$ to 100000 $mm^2$, or more narrowly, 1 to 3 $mm^2$, 1 to 10 $mm^2$, 3 to 10 $mm^2$, 10 to 20 $mm^2$, 20 to 100 $mm^2$, 100 to 1000 $mm^2$, 1000 to 10000 $mm^2$, 10000 to 50000 $mm^2$, or 10000 to 50000 $mm^2$.

The area of the target surface membrane may depend on the disease or condition and the application, eye, epidermis, or internal organ. The area of the drug reservoir surface of the diffusive membrane for contacting a treated area can correspond to the area of a target surface membrane including any of the ranges of the target surface membrane disclosed above.

The step of diffusion into body tissue is achieved by the instillation of small diffusion ports at the base, bottom or nozzle of the delivery apparatus. In one embodiment, these ports are circular with a diameter ranging from 0.01 to 10 mm, from 0.5 mm to 10 mm, or more narrowly, 0.01 to 0.1 mm, 0.1 to 0.3 mm, 0.3 to 0.5 mm, 0.5 mm to 1 mm, 1 mm to 5 mm, or 5 mm to 10 mm. In an embodiment, the surface area of the diffusive membrane can range from 1 $mm^2$ to 100 $mm^2$, or more narrowly, 1 to 5 $mm^2$, 5 to 10 $mm^2$, 10 to 20 $mm^2$, 20 to 50 $mm^2$, 50 to 100 $mm^2$, or greater than 100 $mm^2$. The number of diffusion ports can be 1 to 1,000, or more narrowly, 1 to 10, 10 to 100, 100 to 500, or 500 to 1000, depending on the surface area that is being treated. In another embodiment, an open-cell foam, nanoporous material, or membrane with interconnected channels can be used, which may or may not be flexible and able to conform to the topography of an underlying tissue. In another embodiment, the delivery system may contain one large diffusion port, where, in some cases, the tissue surface may expand to further improve drug delivery. In yet another embodiment, the nozzle of the delivery system may have one or more large diffusion ports with several standoffs to prevent the expansion of tissue into the delivery system.

Using the eye as an example, this invention provides a device and method wherein riboflavin (a drug) is placed on an intact epithelium, and the vacuum application would be applied over a defined surface through a specialized apparatus that causes the riboflavin to permeate uniformly (or, in some cases, discreetly) across the intact epithelium into the corneal stromal tissue at a rate proportional to the magnitude and/or application time of the vacuum applied. This specialized apparatus is comprised of a chamber that simultaneously acts as both a drug reservoir and vacuum. Placing the end surface (nozzle) of the apparatus onto a tissue surface "completes" the chamber, creating a seal which is a substantially air-tight and water-tight seal at the interface of the surface/nozzle with the tissue. A vacuum is then applied to the chamber overlying the tissue, which chamber contains the drug to be diffused. Over time, the vacuum creates negative pressure or negative pressure gradient within the underlying tissue, which in turn, draws the drug-containing fluid into it. Thus, in the foregoing example, the vacuum acts as a driving force for entry of a drug, such as riboflavin, across the epithelium and into the corneal tissue. Because pressure is a scalar quantity rather than a vector quantity, the drug may be forced to diffuse uniformly into the underlying tissue as long as the vacuum is applied, or until complete equilibrium mixing is achieved between the tissue and the solute.

Upon delivery of an effective amount of riboflavin to ocular tissue, the eye may be exposed to radiation such as ultraviolet light to crosslink the tissue exposed to riboflavin. The riboflavin serves as a photosensitizer to create new covalent crosslinks between collagen strands to increase corneal stiffness. This increase in stiffness reduces or prevents progression of ectatic corneal disorders such as keratoconus.

The cross-linking of corneal tissue results in increased prolonged stability for such tissue, and thereby is a treatment for keratoconus. Additionally, a method including vacuum mediated delivery of riboflavin to corneal tissue followed by cross-linking corneal tissue can also be used in other types of treatments. In one embodiment, the method may be applied for preventing regression after corneal tissue has been reshaped, for example, via a subsurface laser treatment, to treat myopia or presbyopia as disclosed in application Ser. No. 13/396,454, now issued as U.S. Pat. No. 9,005,099. In another embodiment, the method may be applied as a way to cross-link corneal tissue solely for the purpose of reshaping the corneal surface to treat myopia or presbyopia.

In a preferred embodiment, the apparatus for delivering the solute to the tissue and creating the vacuum is designed to prevent any suction or backflow of the drug when the vacuum is initiated. This is accomplished through the installation of a proximal or backward flow inhibitor, such as a valve or stepped diffusor in the apparatus or a similar mechanism.

In one embodiment, riboflavin is made to permeate into corneal tissue across the epithelium because of the negative pressure created within the tissue by applying the overlying vacuum. This phenomenon is somewhat counter-intuitive since positive pressure gradients are more often thought of as driving forces for fluids through narrow tubing, for instance. It is well known that the topical application in the absence of a pressure gradient of riboflavin does permeate across the corneal epithelium, but at a very slow rate. Thus, the present invention creates a reverse pressure gradient that greatly accelerates this natural process of diffusion. The delivery of such a drug includes a control element which is achieved by the size and porosity of the delivery device, which can be modulated as accurately as possible. This device may deliver a variety of therapeutic agents over at least several seconds, about one minute, over at least about three minutes, over at least about 10 minutes, over at least about 30 minutes, longer than 30 min if desired or from one to three minutes, three to 10 minutes, 10 to 30 minutes. In a preferred variation, the drug is delivered into tissue in the shortest timeframe. The negative pressure or pulsation of negative pressure as described herein may be maintained during the drug delivery time.

The vacuum delivery system may utilize various therapeutic agents for treating the various diseases or conditions disclosed herein These include, but are not limited to, drugs, such as riboflavin, or its equivalent, which provide a catalyst for cellular activity, anti-infective agents, anti-inflammatory agents, growth-promoters, antiproliferative agents, and combinations thereof. Examples of anti-infective agents include antibacterial agents, antifungal agents and antiseptics. The anti-inflammatory agent may be a non-steroidal anti-inflammatory agent (NSAID) or a steroidal anti-inflammatory agent. The vacuum delivery system may also be used to deliver specialty drugs, such as anti-vascular endothelial growth factor (anti-VEGF) molecules to the posterior segment or the eye, and to deliver chemotherapeutic agents locally to various parts of the body. Exemplary anti-cancer or chemotherapeutic agents include alkylating agents, antineoplastics, anti-metabolites steroids, and bisphosponates. In addition, the vacuum delivery system may be used to deliver the group of medications that use various forms of botulinum toxin (such as Botox®) to temporarily paralyze muscle activity. Additional agents for treating acne include such as retinol and vitamin A derivatives, benzoyl peroxide, and salicylic acid.

The invention can also be directed to delivery of anesthetic or analgesic agents to target surface membranes. A local anesthetic agent is a drug that causes anesthesia, which is a reversible loss of sensation. Analgesic agents are drugs that relieves pain selectively without blocking the conduction of nerve impulses, markedly altering sensory perception, or affecting consciousness. This selectivity is an important distinction between an analgesic and an anesthetic.

Anesthetic agents include, for example, lidocaine, benzocaine, marcaine, and novocaine. Analgesic agents include anti-inflammatory drugs, which alleviate pain by reducing local inflammatory responses. Anti-inflammatory drugs include salicylic acid, pyrazolone, acetaminophen (a derivative of phenacetin), nonsteroidal anti-inflammatory drugs (NSAIDs), and phenacetin (or acetophenetidin). Acetylsalicylic acid, or aspirin, is derived from salicylic acid. NSAIDs) include compounds such as ibuprofen, naproxen, and fenoprofen.

Since the 1980's, with the FDA approval of transdermal patches, the transdermal drug delivery market has grown in excess of $5 billion annually. The skin is a highly specialized organ, with the epidermis providing a safeguard against chemical, microbial and physical attack. These barrier properties of the skin make it a challenging route for the delivery of therapeutic agents. However, one preferred embodiment of the invention herein is to penetrate and thereby provide site specific delivery of drugs through the stratum corneum, which is the outermost layer of the skin and has been identified as the principal barrier for penetration of most drugs. The thickness of this layer is, typically, 10 µm. Because of its ability to cause or accelerate penetration through the stratum corneum, the vacuum delivery system can effectively target the systemic circulation and provide trans-dermal or percutaneous delivery for a wide variety of therapeutic agents, such as vaccines and allergy medications, which normally must be delivered through a needle, orally or through the nasal mucosa.

There are essentially three ways in which a drug molecule can cross an intact stratum corneum. First, the drug can travel through appendages, which include the hair follicle and sweat gland, directly across the stratum corneum barrier. However, these pathways do contain potential resistance because sweat is travelling against the drug diffusion, and sebum from the sebaceous gland may present a barrier. Secondly, the drug can enter the skin through the transcellular route wherein corneocytes provide an aqueous environment for which drugs (especially hydrophilic drugs) can pass. Thirdly, there is the intercellular pathway which involves the drug diffusing through the continuous lipid matrix, which is the most circuitous pathway because the drug must diffuse through repeated aqueous and lipid domains. A particular drug may permeate across the stratum corneum by a combination of these three routes.

In a preferred embodiment, the vacuum delivery system herein may be used to achieve permeation, or augment the delivery of one or more drugs across the stratum corneum utilizing any one, two or all three of the drug penetration pathways mentioned hereinabove, and such delivery can be accomplished without disrupting or damaging any portion of the stratum corneum.

In other preferred embodiments, the vacuum delivery system may also be used to deliver any number of therapeutic agents for treatment of the skin itself (epidermis or dermis) where a disease or condition presents itself within the organ. For example, it can be used for treating neoplasias, inflammatory disorders and microbial infections. Additionally, it could be used to deliver hair-growth agents such as minoxidil or prostaglandins (such as bimatoprost), anti-wart medications, or anti-acne medications such as but not limited to benzoyl peroxide, salicylic acid, antibiotics (such as minocycline and clindamycin), anti-fungals, antivirals, retinoic acid and its derivatives, vitamins (such as vitamin A, C, E), and various photodynamic therapy agents. Anesthetic agents such as lidocaine, and steroids including androgenic and estrogenic steroids or corticosteroids, as well as chemotherapeutic agents to treat solid cancers (including but limited to basal cell carcinoma and squamous cell carcinoma) may also be delivered with the present invention.

In another embodiment, the invention herein may be used to treat various types of tumors, for example on the skin and internal organs. The tumors may be cancerous or benign. An important consideration when treating bone tumors or soft-tissue tumors with chemotherapeutic agents is maintaining a long-acting, localized, yet effectively high concentration of a drug at the site of the tumor cells while producing minimum systemic side effects. Localized chemotherapy delivered on the surface of skin or organ tissue, which can be enabled by the use the vacuum delivery system herein, could reduce the risk of local recurrence at the tumor site, while limiting the toxicity problems associated with traditional systemic chemotherapy.

The vacuum-mediated delivery of anesthetic or analgesic may be used in various ways in methods of surgical treatment on the skin. Embodiments include delivering an anesthetic or analgesic agent for the purpose reducing or eliminating pain during surgery at a target area of skin during a surgical procedure on the skin. For example, the target area may include tumor (e.g., skin cancer) or any other unwanted structure (e.g., wart, birthmark, etc.) targeted for removal by surgery. An exemplary anesthetic may be lidocaine. The lidocaine may be combined with epinephrine or an equivalent.

In one embodiment, a small amount anesthetic or analgesic (e.g., 1 cc) may be delivered into the skin by the vacuum-mediated method at a surgical area targeted for removal. The small amount of anesthetic or analgesic is delivered in order to numb a portion of the surgical area. The width and/or length of delivery area may be from 1 to 20 cm (area of 1 to 400 $cm^2$). The area numbed by the small amount of anesthetic or analgesic may not be large enough for performing the surgery or the amount of anesthetic delivered may not be sufficient for performing the surgery. After the vacuum-mediated delivery, additional anesthetic (e.g., greater than 1 or 2 cc) is delivered by injection at the surgical area in an amount sufficient to perform the surgery so that the surgery can be performed without pain to the patient. The advantage of the vacuum-mediated step prior to injection is that it eliminates the pain to the patient of the needle injection step.

In another embodiment, anesthetic or analgesic is delivered by the vacuum-mediated method to the targeted surgical area that sufficient to allow surgery without use a needle injection of anesthetic. The amount of anesthetic or analgesic (e.g., greater than 1 or 2 cc) and the area of delivery are sufficient to allow the surgery.

In another embodiment, the instant invention may be used to deliver drugs through mucosal membranes, such as those encountered in the gastro-intestinal tract and tongue. Though mucosal membranes are more permeable than, for example, the skin or corneal epithelium, it is difficult to deliver certain drugs through these tissues, such as those with high molecular weights and/or irregular molecular structures.

In another embodiment, this invention may be used to delivery sustained release drugs that have been encapsulated in polymeric mixtures, which can be nanometers in size. Nanotechnology has brought about a fundamental change in manufacturing and is expected to have an enormous positive impact on drug delivery. Some of the salient features of nanoparticles include: 1) small size (e.g., 1 to 1000 microns diameter); 2) high surface area; 3) easy to suspend in liquids; 4) deep access to cells; 5) variable optical and magnetic properties.

The devices used to create the mediated vacuum and thereby deliver the therapeutic agent into the tissue may be created with various designs, but at least include a vacuum capability and a portal system. Additionally, these devices are stable for the purposes of drug administration; they are biocompatible; and, can be produced with certain reproducibility. In one embodiment, the type of vacuum used in the vacuum delivery system can be an electrical pump or a simple syringe. The amount of negative vacuum pressure can vary from 1 to 760 torr. Particularly efficacious negative pressures for accelerating drug delivery may be significantly below 760 torr or ambient pressure. More narrowly, the amount of vacuum or negative pressure may be about 1 torr, about 10 torr, about 100 torr, less than 600 torr, less than 300 torr, less than 100 torr, 1 to 10 torr, 10 to 100 torr, 1 to 300 torr, 10 to 300 torr, 100 to 300 torr, 100 to 200 torr, or 200 to 600 torr. The negative pressure may be constant or maintained at the negative pressure (or vary by less than 10%) during a drug delivery time. This pressure may be applied over a variety of duty cycles, including ones where vacuum is preceded or followed by a "soaking" phase with the therapeutic agent of interest. In this application, tissues are passively exposed to the agent and allowed to re-equilibrate and absorb the adjacent fluid. In another embodiment, a vacuum may be applied after or prior to a topical application of the drug.

In a preferred embodiment, the vacuum created to deliver a solute can be pulsated, wherein a certain pressure is created over the body tissue; it is held for a number of seconds and then released; after a specific number of seconds, the pressure is then reapplied. This pulsation effect enables the drug to diffuse into the tissue faster and more uniformly.

A single pulsation cycle going from a first negative pressure to a second negative pressure and back again to the first negative pressure, referred to herein as the "cyclic rate" can take from about 1 second to about 20 minutes, preferably at present, from about 5 seconds to about 20 seconds, about 10 seconds to about 15 seconds. A pulsation range, i.e., first negative pressure to second negative pressure, may be 1 to 760 torr, 10 to 760 torr, 100 to 760 torr, 1 to 600 torr, 100 to 600 torr, 10 to 100 torr, or 100 to 400 torr.

In another embodiment, positive pressure may be used in combination with the negative pressure. The amount of positive pressure can vary from 1 to 600 psi above ambient pressure. In certain aspects, the positive pressure can be 1 to 3 psi, 3 to 10 psi, 10 to 20 psi, 20 to 50 psi, 50 to 100 psi, or greater than 100 psi above ambient pressure or 760 torr. In certain aspects, alternating positive and negative pressure is applied in a pattern or in sequence. In some aspects, a process can include decreasing the pressure to a negative pressure and increasing the pressure to a positive pressure. The pressure can then be returned to ambient or the above process can be repeated one or more times.

The type of apparatus used in this invention may take various forms, but are generally designed to have a size and shape appropriate for the intended drug delivery into the targeted tissue. Thus, the form (i.e., size and shape) is dictated by two factors: first, the surface area of the tissue that the device needs to reach and to which the drug is delivered; second, the shape of the tissue surface upon which the device is to be sealed in order to deliver the drug. For example, the eye's cornea has a diameter of approximately 12 mm and a radius of curvature of approximately between 6 and 9 mm (typically 7.8 mm anteriorly and 6.5 mm posteriorly), and these measurements are reflected in FIGS. 1-8.

A wide range of drugs may be formulated for delivery to body tissues with the vacuum delivery system of this invention. The drug may be selected from suitable proteins, peptides and fragments thereof, which can be naturally occurring, synthesized or recombinantly produced. Additionally, the drugs can be in nanometer size.

The types of solutes that can be included in the vacuum delivery system are set forth, but are not limited to those expressly mentioned herein and those in U.S. Pat. No. 7,918,814 by Prausnitz et al., which is incorporated as if fully set forth herein.

Figure 1:
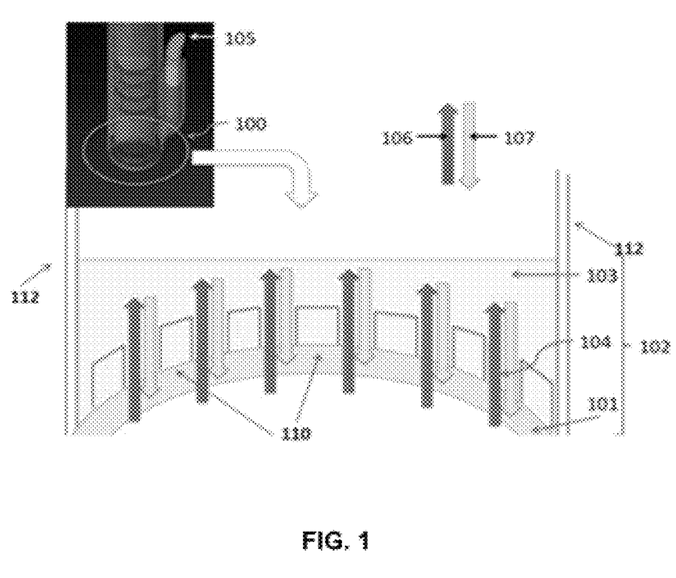
FIG. 1 is a schematic setting forth the mechanism of action of a vacuum delivery system.

FIG. 1 shows a prototype schematic of the mechanism of action of the present invention as it applies to the eye. A cross section of the vacuum tip 100 is shown in contact with the cornea 101. The vacuum tip 100 includes outer walls 112 and a distal perforated base 110 having pores or perforations 104. The base 110 has a curved, concave outer surface configured to fit over cornea surface. The outer surface of base 110 is further configured to create an airtight seal when placed in contact with the cornea surface. The outer surface of the base 110 is positioned in contact with the cornea surface, creating a reservoir 102 for a drug, such as riboflavin, 103 bounded or enclosed by the cornea surface and the outer walls 112. The pores 104 of the vacuum tip allow for the drug solution 103 that is injected in through the fluid port 105. Application of vacuum pull 106 (negative pressure) over-lying the drug solution creates pressure gradient between the drug solution 103 and the cornea 101. This vacuum application causes the drug to diffuse 107 into the cornea in an accelerated fashion across its outer layer (epithelium) without the need for debridement of the epithelium.

The device and method herein were tested to verify the effectiveness of the vacuum delivery system and to quantify concentrations of the standard formulation of riboflavin that is used in the process of cross-linking collagen corneal tissue in rabbit corneas. The tests employed the present invention to facilitate trans-epithelial delivery of riboflavin at varying application time periods, and compare the concentrations achieved with the concentration of riboflavin achieved through the standard method of riboflavin delivery (i.e., in which the epithelium is surgically removed). Testing performed suggests that the present invention increases riboflavin delivery to the cornea to a degree equivalent to the effect of removing the corneal epithelium. In other embodiments, high levels of vacuum, higher riboflavin concentrations, and the use of penetration enhancers may be used to increase the amount of riboflavin diffusion into the cornea per unit time. These animal studies clearly provide a proof of principle for the efficacious delivery of riboflavin into the cornea, through an intact epithelium, using the device and method of this invention. These studies also provide critical concentration/treatment time data for utilizing this invention.

Drugs noninvasively delivered into the body through barrier membranes can be done using various vacuum mediated delivery devices. These devices may be constructed in a multitude of sizes and shapes. The device generally includes a vacuum attachment on the proximal end of a handle, which attachment can be in the form of a syringe or vacuum generating instrument. In some embodiments, the device may have a vacuum gage. A proximal or backward flow inhibitor, such as a valve or stepped diffusor is typically included to keep solutes from being retracted by the applied vacuum. The distal portion of the device may be variously shaped and angulated to facilitate positioning so that the area of solute delivery can be adequately covered. There is generally a solute inlet just above the surface area of the device and this enables the solute to be placed in a vacuum chamber and in contact with the surface area where the drug is targeted for delivery. For purposes of pulling a vacuum on the surface area of the targeted membrane, it is preferable that the distal end of the device create an air-tight seal on such membrane. The device may contain a series of small ports on the distal end through which the solute is diffused uniformly through the barrier membrane and into the targeted tissue. When needed for convenience of application, the device may include handles on the perimeter surface. The device may be made from any biocompatible material including, but not limited to, polymers, e.g., polyethylene and copolymers thereof, polyethylene terephthalate or copolymers thereof, nylon, silicone, polyurethanes, fluoropolymers, poly-vinylchloride, polyamides, acrylics, and combinations thereof, depending on the amount of flexibility or stiffness desired. It may also be made out of metals such as aluminum, titanium, or stainless steel, or alternatively out of ceramic or porcelain.

The device may be specifically designed for a solute that has been formulated to treat a particular disease or condition. Further, the design is intended to fit the anatomy to which the device is being attached for the solute delivery. Once the device has delivered the solute, over whatever time period is necessary, the vacuum seal is released and the device removed from the target membrane.

Figure 2:
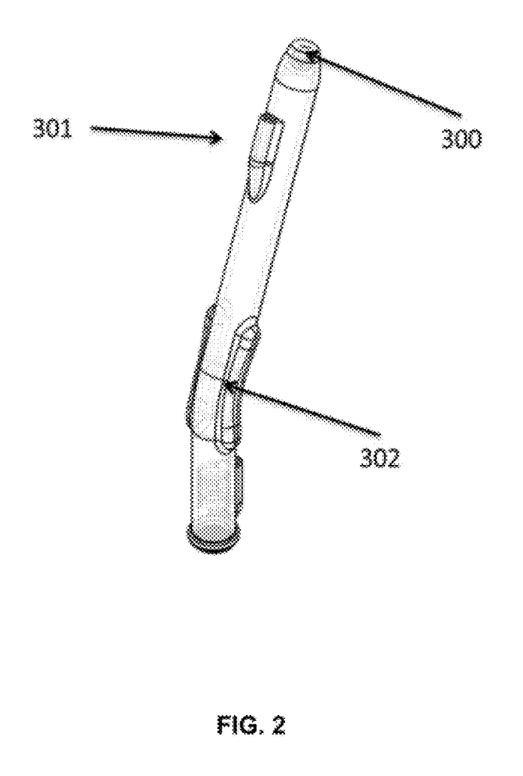
FIG. 2 is a drawing of the side of the device. Handles are on the radii of the curve. The vacuum tube is on the proximal end of the handle.

FIG. 2 shows an example of a device for delivering riboflavin through an intact epithelium into the cornea. The device has the form or shape of a handle with a curve. The figure illustrates where the vacuum line is attached 300 on the proximal end of the handle. There is an inlet for the vacuum gauge 301 between the proximal and distal end of the handle, and the grasping handles 302 are located on the radii of the curve of the handle.

Figure 3:
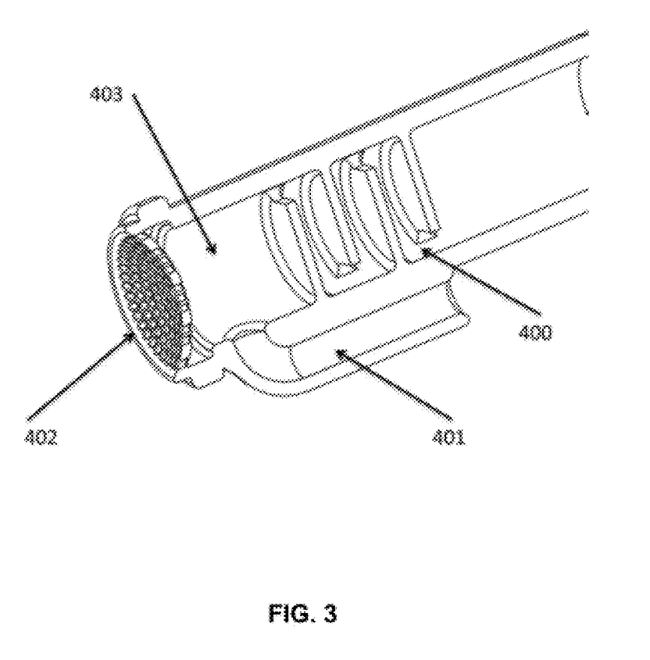
FIG. 3 is a cut-out view through the center axis. The proximal or backward flow inhibitor or stepped diffusor is shown which keeps solutes from being retracted by the applied vacuum. The solute inlet is just above the perforated contoured surface that is in contact with the surface of the eye. This portion of the device is called the nozzle.

FIG. 3 is a cut-out view of the distal end of the device in FIG. 2 through the center axis. The stepped diffusor 400 keeps solutes from being retracted by the applied vacuum. The stepped diffusor may include a flow valve or similar device to prevent back flow. The solute inlet 401 is above a perforated contoured surface 402 which is configured to be in contact with the surface of the eye. The solute reservoir and vacuum chamber 403 abut the contoured surface 402.

Figure 4:
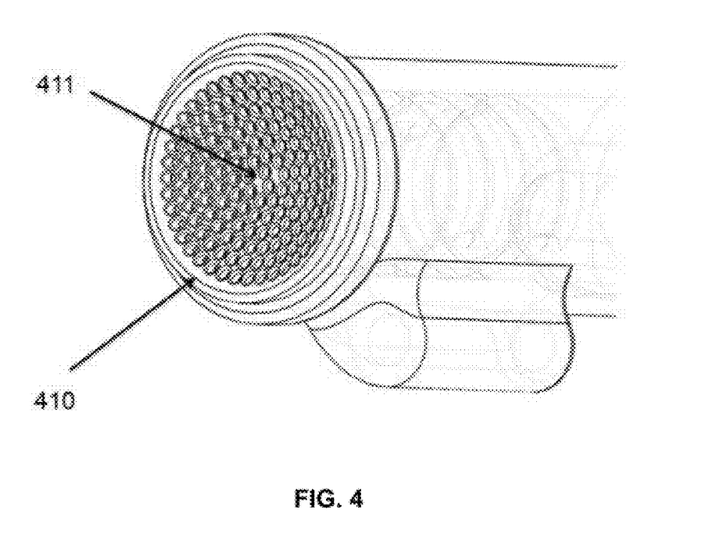
FIG. 4 shows a nozzle design with at least 250 ports to provide uniform delivery of the solute.

FIG. 4 shows a nozzle design of a distal end of the device in FIG. 2 with a curvature or curved rim 410 and has at least 250 ports 411 to provide uniform delivery of the solute.

Figure 5:
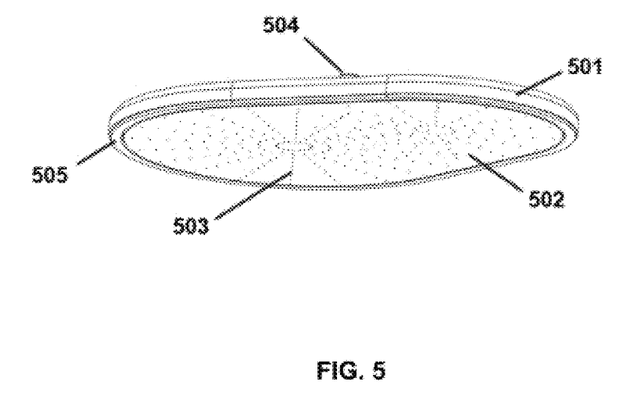
FIG. 5 shows an example of a vacuum delivery system that may be applied to the skin to facilitate the delivery of one or more drugs.

FIG. 5 shows an example of the distal portion of the vacuum delivery system as it applies to the skin. The main body 501 contains an inner cavity (not shown) that may serve as a reservoir for the drug or drug solution. The diffuse or diffusion membrane 502 contains holes or pores 503 and is in direct contact with the tissue. The drug may permeate through the pores 503 and, thus, be exposed to the tissue (i.e., skin). Vacuum is pulled via a vacuum port 504. The diffuse membrane may be adhered to the main body 501 by an adhesive band 505. Optionally, the main body 501 may contain a fluid port (not shown) for the injection of drug into the inner cavity.

Figure 6:
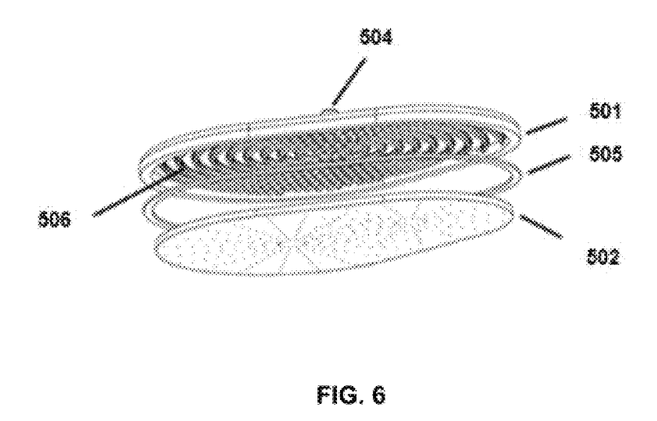
FIG. 6 is an exploded view of a vacuum delivery system that may be applied to the skin to facilitate the delivery of one or more drugs.

FIG. 6 is an expanded view of the example of the distal portion of the vacuum delivery system shown in FIG. 5. Protrusions or volumetric supports 506 inside the main body 501 may prevent the diffuse membrane 502 from collapsing into the main body 501 when a vacuum is created via the vacuum port 504. Volumetric supports 506 also are arranged to distribute drug solution uniformly over the area of the diffusion membrane 502.

Figure 7:
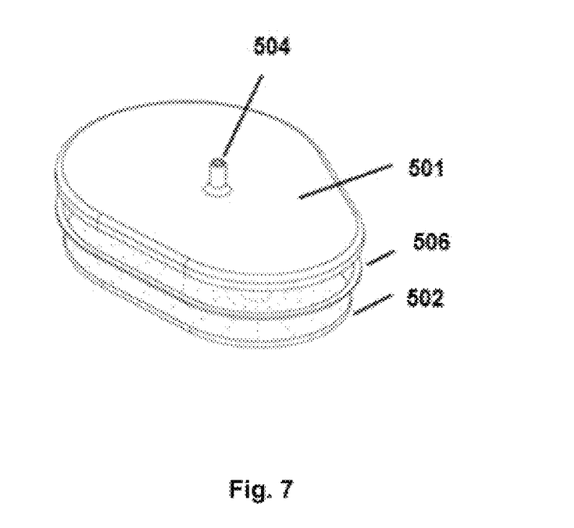
FIG. 7 shows a top exploded view of a vacuum delivery system that may be applied to the skin to facilitate the delivery of one or more drugs.

FIG. 7 is a top exploded view of the distal portion of the vacuum delivery system shown in FIG. 5.

Figure 8:
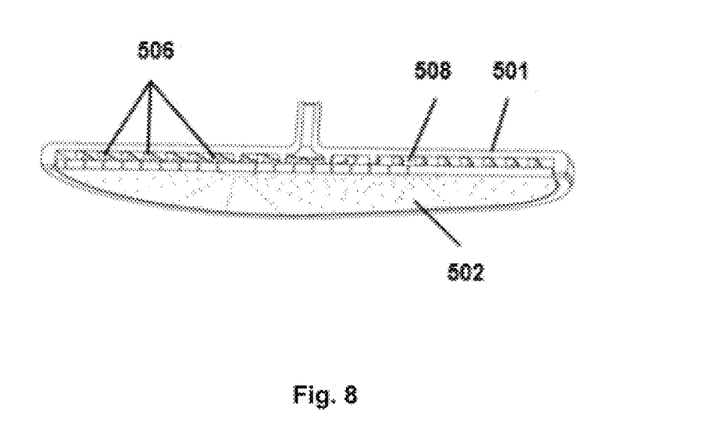
FIG. 8 shows cross-sectional view of a vacuum delivery system that may be applied to the skin to facilitate the delivery of one or more drugs.

FIG. 8 is a cross-sectional view of the example of the distal portion of the vacuum delivery system shown in FIG. 5 that shows the volumetric supports 506 supporting the diffuse membrane 502. The inner cavity 508 between the main body 804 and the diffuse membrane 802 may serve as a reservoir for the drug or drug solution.

Figure 9:
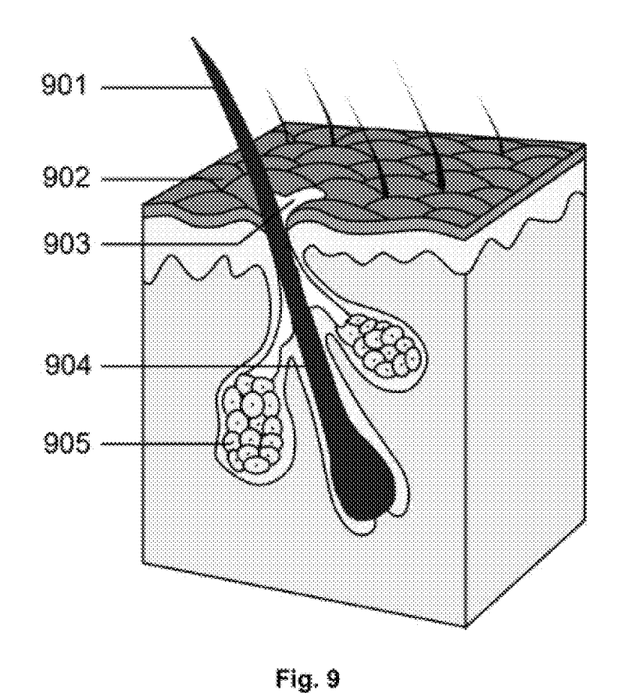
FIG. 9 shows cross-sectional view of a skin anatomy.

FIG. 9 is a depiction of the human skin anatomy. The diagram shows the sebaceous gland 905 releasing sebum 903 through a pore and onto the surface of the skin 902. Due to the tortuous path created by the hair 901 and follicle 904 structures, as well as the small pore and duct sizes, is it difficult to deliver drug into the sebaceous gland 905 from the surface of the skin.

Figure 10:
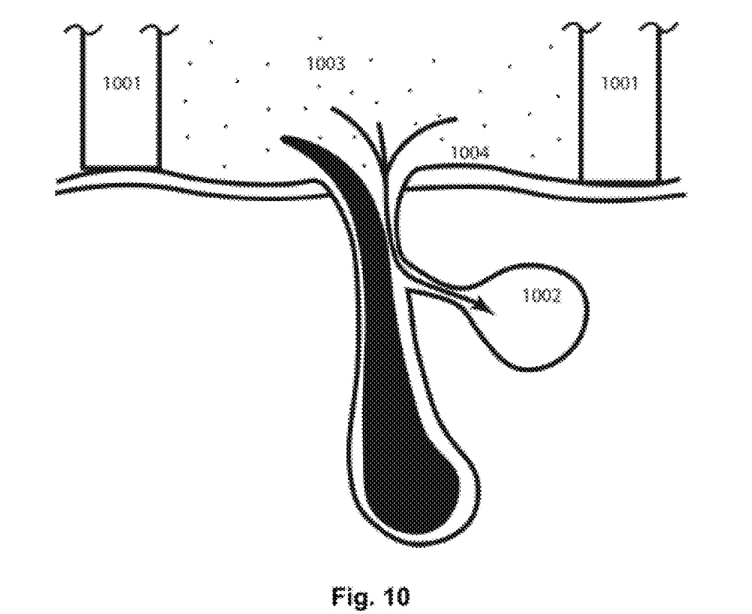
FIG. 10 shows cross-sectional view of a vacuum delivery system applied to the skin to facilitate the delivery of one or more drugs into a sebaceous gland.

FIG. 10 shows an embodiment of the vacuum delivery system 1001 delivering drug 1003 into the sebaceous gland 1002. The vacuum delivery system 1001 creates a seal between itself and the skin surface 1004.

Factors that may influence the drug penetration through a body membrane, when utilizing the device and method of this invention, include such characteristics as the size of the drug particles and cell density or structure of the membrane.

The therapeutic agent may be delivered through a membrane barrier in a short time period, including, but not limited to, about 1 second, about 10 seconds, about 20 seconds, about 3 minutes, about 10 minutes, about 20 minutes, at about 30 minutes, about 40 minutes or about 1 hour.

The amount of vacuum applied is conditioned upon the type and location of the membrane being penetrated, e.g., the eye is highly sensitive to increases in intraocular pressure (IOP); therefore, the vacuum for drug delivery into the cornea will be sufficiently low enough to prevent any adverse increase in IOP. Such a high degree of sensitivity is not experienced in the application of vacuum delivery to other body organs, such as the skin.

The amount of vacuum and time intervals or pulsation utilized with the drug delivery system can have a material effect on achieving the delivery goals for a specific drug. The drug delivery for the invention herein has been tested with a variety of pulsated times.

The drugs delivered through barrier membranes by application of this invention may further include components such as preservatives, buffers, binders, disintegrants, markers, lubricants, and any other penetration enhancing excipients that can assist in the penetration of the respective membranes. Furthermore, the drug may be placed in a pharmaceutically acceptable carrier, e.g., when the drug is encapsulated in microparticles or nanoparticles, to form a suspension, such as a semi-solid gel.

The concept underlying the devices and methods described herein may be used to treat a vast array of diseases and conditions. These will include anywhere in the body where there is a need to penetrate a barrier membrane for the purpose of delivering a drug for site specific treatment or to provide a conduit or reservoir for continuous release of a drug over a predetermined time. For the eye, these devices may be used to deliver drugs for treatment of diseases and conditions in any part of the anterior segment, and such drugs would include anti-microbials, anti-inflammatories, and analgesics. Examples of antimicrobials include but are not limited to fluoroquinolones, vancomycin, cephalosporins, macrolides, or aminoglycosides that are needed for the treatment of bacterial ulcers or keratitis. Anti-fungals may also be used to treat fungal infections. In addition, the devices may also be effective in delivering drugs that could migrate into the posterior segment for treatment of diseases such as macular degeneration and uveitis, plus providing the opportunity for gene therapy delivery to back of the eye.

Furthermore, the devices may enable trans-dermal delivery of vaccines by providing penetration of agents through the epidermal layer of the skin. Additionally, the devices can be used to treat skin conditions such as skin cancers and acne. Plus, the devices can deliver solutes that provide cosmetic treatment for the skin, including delivery to deeper structures such as hair follicles (to treat hair loss), sebaceous glands (to treat acne), and even muscle (in the case of Botox®).

In general, the present invention may be effective to deliver drug to various layers, structures, or regions of the skin including the epidermis, papillary dermis, dermal papillae, dermis, subcutis/hypodermis, subcutaneous fat, sudoriferous gland, recticular dermis, sweat ducts, eccrine sweat gland and duct, hair follicle, and arrector pili muscle.

Because the devices can be sized to fit any barrier membrane area, they can be used to deliver chemotherapeutic agents for site specific cancer treatment in many parts of the body.

Although the invention set forth herein has been described in some detail by way of illustration and example for purposes of clarity of understanding, it will be readily apparent to those of ordinary skill in the art in light of the teachings of this invention that certain changes and modifications may be made thereto without departing from the spirit and scope of the appended claims.

What is claimed:

1. A method for delivering a drug into a tissue of a patient non-invasively for treating a disease or condition in the patient in need thereof, comprising:
    placing a surface of a drug reservoir in contact with an epithelial or surface of the tissue to which the surface of the drug reservoir has been conformed such that an air-tight contact between the drug reservoir surface and the epithelial or surface of the tissue is formed and such that a fluid in the drug reservoir is placed in fluid communication through the surface of the drug reservoir with the epithelial or surface of the tissue; and
    creating a vacuum within the drug reservoir without disrupting the tissue and to effect diffusion of the fluid in the drug reservoir through the epithelial or surface of the tissue and into the subsurface of the tissue.

2. The method of claim 1, wherein the surface of the tissue is the epithelial surface.

3. The method of claim 2, where the fluid comprises a substance that is capable of catalyzing the cross-linking of macromolecules in the tissue.

4. The method of claim 1, wherein the fluid comprises an anti-microbial, an anti-inflammatory, an analgesic, antiseptic, or an anti-VEGF drug.

5. The method of claim 1, wherein the delivery of a drug is for the treatment of uveitis, keratoconus, glaucoma, dry eye, diabetic macular edema, age-related macular degeneration, corneal infection or cytomegalovirus retinitis.

6. The method of claim 1, wherein the vacuum is a pressure between 1 and 100 torr.

7. A method for delivering a drug into the skin of a patient for treating a disease or condition in the patient in need thereof, comprising:
    placing a surface of a drug reservoir in contact with a skin surface to which the surface of the drug reservoir forms an air-tight contact between the drug reservoir surface and the skin surface and such that a fluid in the drug reservoir is placed in fluid communication through the surface of the drug reservoir with the skin surface; and
    creating a vacuum within the drug reservoir without disrupting the skin and to effect diffusion of the fluid in the drug reservoir through the skin surface and into a subsurface of the skin.

8. The method of claim 7, wherein the drug is delivered into a sebaceous gland.

9. The method of claim 8, wherein the drug is delivered through epidermal, dermal, and/or subcutaneous layers of the skin.

10. The method of claim 7, wherein the drug is delivered into a bloodstream.

11. The method of claim 7, wherein the drug is delivered into a sweat gland.

12. The method of claim 7, wherein a vacuum is used to increase extracellular space and/or pore sizes within the skin prior to drug diffusion into the skin.

* * * * *